United States Patent [19]
Lam

[11] Patent Number: 5,868,777
[45] Date of Patent: Feb. 9, 1999

[54] METHOD FOR REPAIRING A BIFURCATED VESSEL

[75] Inventor: Sharon Lam, San Jose, Calif.

[73] Assignee: Advanced Cardiovascular Systems, Inc., Santa Clara, Calif.

[21] Appl. No.: 811,125

[22] Filed: Mar. 3, 1997

Related U.S. Application Data

[62] Division of Ser. No. 677,248, Jul. 9, 1996, Pat. No. 5,607,444, which is a continuation of Ser. No. 162,579, Dec. 2, 1993, abandoned.

[51] Int. Cl.⁶ .................................................. A61M 29/00
[52] U.S. Cl. ............................................................ 606/194
[58] Field of Search .................................... 606/194, 195, 606/198, 191–193, 108; 623/1, 12; 604/281, 104, 105, 106

[56] References Cited

U.S. PATENT DOCUMENTS

| | | | |
|---|---|---|---|
| 3,397,699 | 8/1968 | Kohl | 606/194 |
| 4,793,348 | 12/1988 | Palmaz | 606/194 |
| 5,064,435 | 11/1991 | Porter | 623/12 |
| 5,085,664 | 2/1992 | Bozzo | 606/191 |
| 5,197,978 | 3/1993 | Hess | 623/1 |
| 5,222,971 | 6/1993 | Willard et al. | 606/158 |
| 5,226,913 | 7/1993 | Pinchuk | 623/1 |
| 5,234,457 | 8/1993 | Andersen | 606/198 |
| 5,628,783 | 5/1997 | Quiachon et al. | 606/194 |

*Primary Examiner*—Michael Buiz
*Assistant Examiner*—Vikki Trinh
*Attorney, Agent, or Firm*—Fulwider Patton Lee & Utecht, LLP

[57] ABSTRACT

A method and apparatus for repairing a vessel at a bifurcation without obstructing blood flow through the bifurcation, wherein an expandable ostial stent comprises a tubular body and a deformable flaring portion. Repair of a bifurcated vessel is accomplished by positioning the expandable ostial stent within a diseased portion of the bifurcation so that the flaring portion caps the ostium and the tubular body is seated within a side branch to the bifurcation, thereby completely repairing the vessel at the bifurcation without occluding blood flow.

2 Claims, 5 Drawing Sheets

METHOD FOR REPAIRING A BIFURCATED VESSEL

This application is a divisional of U.S. Ser. No. 08/677,248, filed Jul. 9, 1996, which will issue as U.S. Pat. No. 5,607,444 on Mar. 4, 1997, which is a continuation of U.S. Ser. No. 08/162,579, filed Dec. 2, 1993, now abandoned.

BACKGROUND OF THE INVENTION

1. Field of the Invention

The invention relates to a stent for use at a bifurcation and, more particularly, an expandable and deformable stent which is particularly useful for repairing bifurcated blood vessels that are diseased, and a method or apparatus for implantation.

2. Prior Art

Stents conventionally repair blood vessels that are diseased and are generally hollow and cylindrical in shape and have terminal ends that are generally perpendicular to its longitudinal axis. In use, the conventional stent is positioned at the diseased area of a vessel and, after placement, the stent provides an unobstructed pathway for blood flow.

Repair of vessels that are diseased at a bifurcation is particularly challenging since the stent must overlay the entire diseased area at the bifurcation, yet not itself occlude blood flow. Therefore, the stent must, without occluding blood flow, overlay the entire circumference of the ostium to a diseased portion and extend to a point within and beyond the diseased portion. Where the stent does not overlay the entire circumference of the ostium to the diseased portion, the stent fails to completely repair the bifurcated vessel. Where the stent overlays the entire circumference of the ostium to the diseased portion, yet extends into the junction comprising the bifurcation, the diseased area is repaired, but blood flow is occluded in other portions of the bifurcation. Moreover, by extending into the junction comprising the bifurcation, the stent may block access to portions of the bifurcated vessel that require performance of further interventional procedures.

Conventional stents are designed to repair areas of blood vessels that are removed from bifurcations and, since a conventional stent generally terminates at right angles to its longitudinal axis, the use of conventional stents in the region of a vessel bifurcation may result in blocking blood flow of a side branch or fail to repair the bifurcation to the fullest extent necessary. The conventional stent might be placed so that a portion of the stent extends into the pathway of blood flow to a side branch of the bifurcation or extend so far as to completely obstruct blood flow in a side branch. The conventional stent might alternatively be placed proximal to, but not entirely overlaying the circumference of the ostium to the diseased portion. Such a position of the conventional stent results in a bifurcation that is not completely repaired. The only conceivable situation that the conventional stent, having right-angled terminal ends, could be placed where the entire circumference of the ostium is repaired without occluding blood flow, is where the bifurcation is formed of right angles. In such a scenario, extremely precise positioning of the conventional stent is required. This extremely precise positioning of the conventional stent may result with the right-angled terminal ends of the conventional stent overlying the entire circumference of the ostium to the diseased portion without extending into a side branch, thereby completely repairing the right-angled bifurcation.

To circumvent or overcome the problems and limitations associated with conventional stents in the context of repairing diseased bifurcated vessels, a stent that consistently overlays the entire circumference of the ostium to a diseased portion, yet does not extend into the junction comprising the bifurcation, may be employed. Such a stent would have the advantage of completely repairing the vessel at the bifurcation without obstructing blood flow in other portions of the bifurcation. In addition, such a stent would allow access to all portions of the bifurcated vessel should further interventional treatment be necessary.

SUMMARY OF THE INVENTION

The invention provides an ostial stent that completely repairs a vessel at a bifurcation without obstructing blood flow in other portions of the bifurcation, thereby allowing access to all portions of a bifurcated vessel should further interventional treatment be necessary. The invention also provides a method and apparatus for implanting the ostial stent.

The present invention is based on utilization of an ostial stent comprising an expandable tubular body and an end portion that is capable of being flared. To achieve the desired result of completely repairing a bifurcated vessel without occluding blood flow, the ostial stent is placed within the bifurcated vessel with its flaring portion, flared open, at the ostium to the diseased portion and tubular body of the ostial stent extending within and beyond the diseased portion.

The tubular body of the ostial stent capable of radial expansion. That is, the cross-sectional area of the ostial stent may be increased. The tubular body may comprise a geometric pattern or structural configuration that facilitates the radial expansion. In a preferred embodiment, the cross-sectional area is increased by means of exerting force upon the internal walls comprising the tubular body.

It is contemplated that the tubular body have adequate radial strength since the tubular body must have sufficient radial strength so that it retains its pre-expanded cross-sectional area, and after radial expansion, have sufficient radial strength so that it retains its expanded cross-sectional area. Adequate radial strength may be accomplished in part through the geometric structural configuration chosen for the tubular body and in part through the selection of material comprising the tubular body. Regarding the material of the tubular body, it is contemplated that the material have a low metal-to-space ratio.

The flaring portion of the ostial stent is continuous from the tubular body and it may be comprised of the same material as the tubular body, or the materials may differ. In addition, the flaring portion and tubular body may be formed as one piece or comprise two or more separate and distinct parts which have been attached.

The flaring portion is capable of expanding and may embody a plurality of individual petals that are each individually capable of adopting an undeformed configuration that is substantially parallel to the longitudinal axis of the stent and a deformed configuration that is unparallel to and at some angle slanting away from the longitudinal axis. It is contemplated that the flaring portion be capable of deforming throughout its length to varying degrees so that the flaring portion conforms to the irregular walls comprising an ostium. It is also contemplated that the individual petals may be connected by a thin malleable material that enhance the conforming capability of the flaring portion. In the alternative, the flaring portion may embody material that accomplishes the flaring function, yet has no recognizable pedals. In a preferred embodiment, deformation of the flaring portion may be accomplished by exerting a force upon the inside walls comprising the flaring portion.

It is also contemplated that radiopaque markers be formed in or attached to the ostial stent and placed so as to mark the joining line between the flaring portion and the tubular body. In addition, radiopaque markers could be placed to mark the circumferential location of each of the pedals that form the flaring portion. Marking the ostial stent in this way facilitates proper placement and orientation of the ostial stent within the bifurcated vessel.

Placement of the ostial stent within a diseased bifurcated vessel involves radially expanding the tubular body and expanding and deforming the flaring portion and may be useful in unobstructing occluded vessels or attaching the ostial stent in the area of an aneurysm. Radial expansion of the tubular body allows it to substantially conform, where necessary, to the inner walls of the bifurcated vessel, thereby seating the ostial stent within the bifurcated vessel. The flaring portion is deformed so that it substantially conforms to and "caps" the ostium to the diseased portion of the bifurcation, thereby resulting in firmly securing the ostial stent at the bifurcation.

Deployment of the ostial stent can be accomplished through the utilization of balloon catheters. The ostial stent is loaded onto the balloon of a balloon catheter with the flaring portion of the ostial stent configured to be unexpanded and substantially parallel to the longitudinal axis of the ostial stent and the tubular body in an unexpanded configuration. The ostial stent may be placed on the balloon so that its flaring portion is loaded on the distal portion of the balloon, and the tubular body is loaded on the proximal portion of the balloon. It is also contemplated that, depending upon the application, the ostial stent may be placed upon the balloon with its flaring portion located on the proximal end of the balloon and its tubular body loaded on the distal portion of the balloon.

The balloon catheter loaded with the ostial stent is advanced to the location of the diseased bifurcated vessel and by means of radiography, precise positioning of the ostial stent is achieved. Through the use of radiography, the location of the radiopaque markers which mark the ostial stent, can be ascertained and the ostial stent can be precisely positioned within a vessel.

After the ostial stent is positioned within the diseased bifurcated vessel, balloon catheters are employed to secure the ostial stent in position. By expanding the balloon carrying the ostial stent, the tubular body is seated within the diseased portion of the bifurcated vessel extending away from the bifurcation and the flaring portion is configured to "cap" the ostium to the diseased portion of the vessel. In the alternative, a series of various sized and shaped balloon catheters can be employed to configure the ostial stent so that it seats within and "caps" the ostium to the diseased portion of the bifurcation or a bi- or tri-balloon system may be employed to properly implant the tubular body and flaring portion of the ostial stent.

In another embodiment of the invention, the tubular body and flaring portion are fabricated from a memory-retaining metal, such as Nickel-Titanium (NiTi). At a cold temperature, the tubular body would be in an unexpanded condition, and the flaring end would be unexpanded and substantially parallel to the longitudinal axis of the ostial stent. At an increased temperature, the tubular body expands to seat within the diseased portion of the bifurcated vessel, and the flaring portion expands and deforms to "cap" the ostium to the diseased portion of the bifurcation. At a patient's normal body temperature, the ostial stent retains an expanded and deformed configuration, thereby sustaining a seated and "capped" position within the bifurcated vessel.

Advancement of a memory-retaining ostial stent to a diseased bifurcated vessel can be accomplished by means of a balloon catheter. During advancement, the memory-retaining stent can be maintained at a cold temperature. Thereafter, the stent would be subjected to an increased temperature so that the stent takes its expanded end deformed configuration.

It is also contemplated that only a portion of the ostial stent comprises memory-retaining material. Deformation or expansion of the portion of the ostial stent that is not memory-retaining may be achieved by means of balloon expansion.

In another embodiment, the ostial stent is comprised of spring-like material and is loaded in a retaining sleeve so as to place the tubular body in an unexpanded configuration and the flaring portion in a configuration that is unexpanded and substantially parallel to the longitudinal axis of the ostial stent. Upon removal of the retaining sleeve, the tubular body expands and the flaring portion opens, thereby securing the ostial stent within the diseased portion of the bifurcated vessel.

Advancement of the spring-like ostial stent to the site of a diseased bifurcated vessel may also be accomplished by a balloon catheter. In this embodiment, the spring-like ostial stent may be placed within a retaining sleeve and loaded upon the balloon of the balloon catheter. After advancement of the spring-like ostial stent to the site of the diseased bifurcated vessel, expansion of the tubular body and expansion and deformation of the flaring portion is achieved by removing the retaining sleeve.

It is also contemplated that only a portion of the ostial stent comprises spring-like material. Deformation or expansion of the portion of the ostial stent that is not comprised of spring-like material may be accomplished by means of balloon expansion.

Other features and advantages of the present invention will become apparent from the following detailed description, taken in conjunction with the accompanying drawings, which illustrate, by way of example, the principles of the invention.

DETAILED DESCRIPTION

Figure 1:
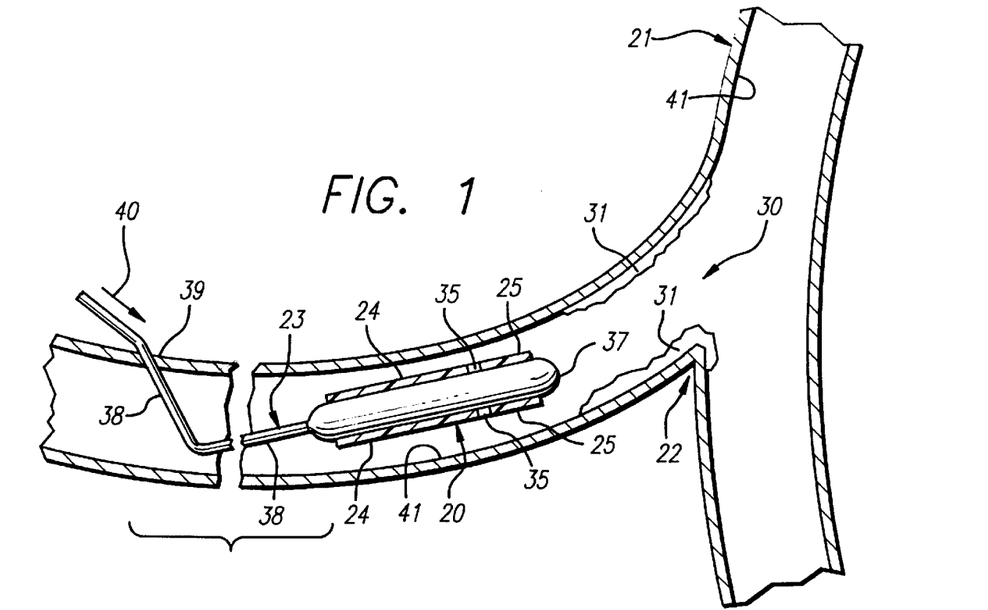
FIG. 1 depicts a partial cross-sectional view, illustrating an ostial stent loaded upon a balloon catheter during advancement of the ostial stent to the site of a diseased bifurcated vessel.

As is shown in the drawings, which are included for purposes of illustration and not by way of limitation, the invention is embodied in an ostial stent 20 (FIG. 1) and provides means to completely repair a diseased blood vessel 21 at a bifurcation 22. Conventional stents are limited in structure to completely repair diseased blood vessels at a bifurcation. Placement of conventional stents in the region of a bifurcation for the purpose of repairing a diseased vessel may result in the conventional stent not entirely repairing the diseased region or the conventional stent extending into the junction comprising the bifurcation, thereby obstructing blood flow. The ostial stent 20 of the present invention is capable of completely repairing a diseased bifurcated vessel 21 without obstructing blood flow in the other portions of the bifurcation 22. Thus, the ostial stent provides a patient with superior means to repair a diseased bifurcated vessel 21 and leaves the bifurcated vessel 21 in a condition amenable to further interventional procedures.

The present invention (FIG. 1) accomplishes complete repair of a diseased vessel 21 at its bifurcation 22 by means of its novel structure and method of deployment. The dimensions and characteristics of the ostial stent 20 are selected to assure proper placement within and complete repair of the diseased bifurcated vessel 21. Similarly, the dimensions and characteristics of the deployment mechanism utilized to deploy the ostial stent 20 are dependent upon the application.

Figure 2:
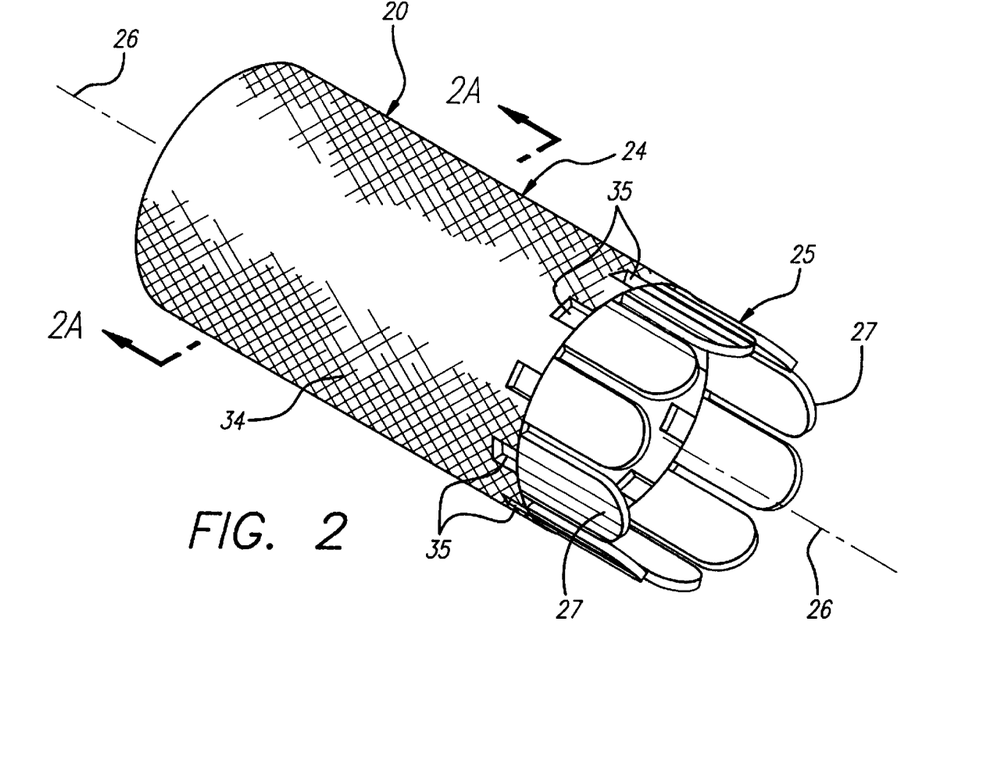
FIG. 2 depicts a perspective view of one embodiment of the present invention, illustrating an ostial stent in an unexpanded and undeformed configuration.
Figures 2A, 3:
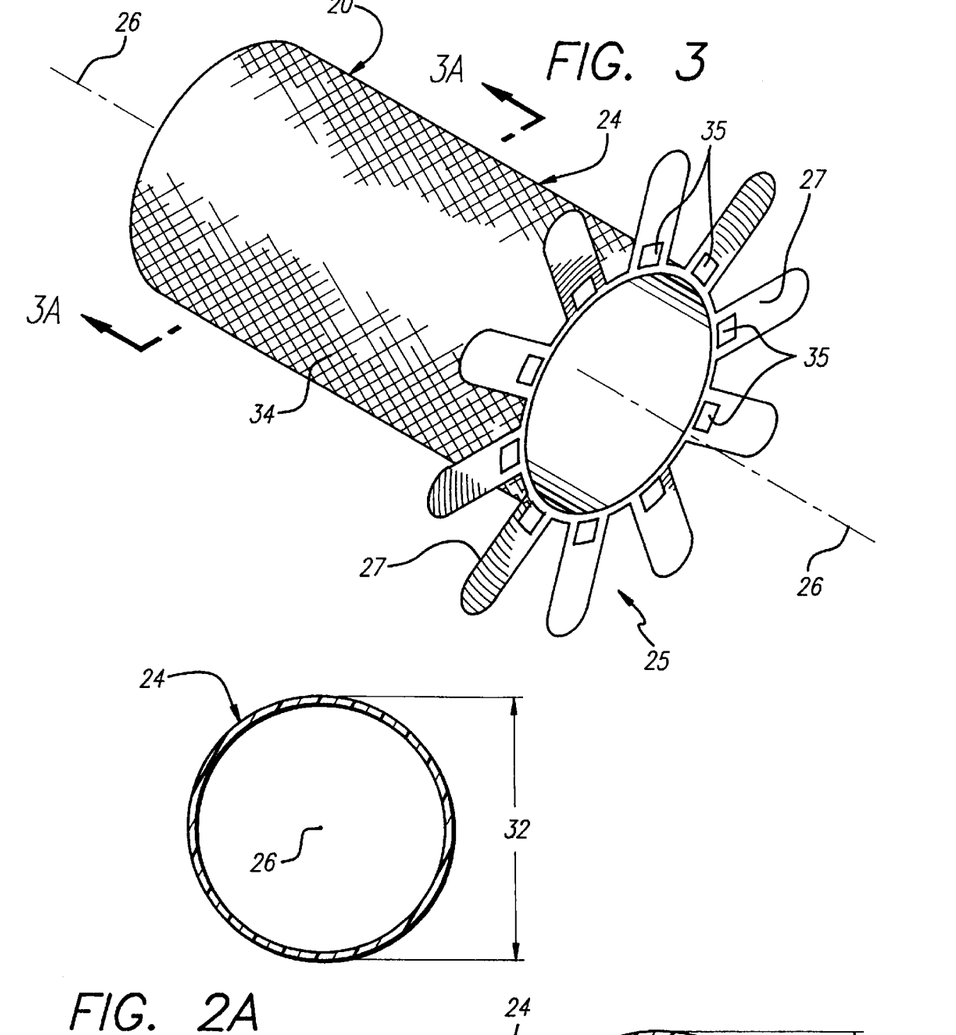
FIG. 2a illustrates a cross-sectional view taken along line 2a—2a of an unexpanded and undeformed ostial stent.
FIG. 3 depicts a perspective view of one embodiment of the present invention, illustrating an ostial stent in an expanded and deformed configuration.

The ostial stent 20 (FIG. 2) has a tubular body 24 and a flaring portion 25 and may be comprised of one piece or two or more connected parts. The flaring portion 25 is continuous from and may be greater than, less than, or equal in length to the tubular body 24 of the ostial stent. In FIGS. 2 and 3 and by way of example, the flaring portion 25 is shown to be less in length than the tubular body 24.

Figure 3A:
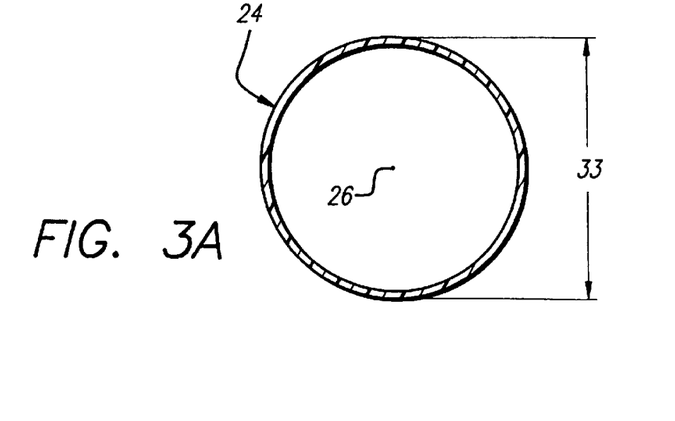
FIG. 3a illustrates a cross-sectional view taken along line 3a—3a of an expanded and deformed ostial stent.

The material and structure of the ostial stent 20 is selected so that the ostial stent 20 is expandable and has sufficient radial strength to retain its shape. The material of the tubular body 24 may be the same as that chosen for the flaring portion 25, or the material may differ. Irrespective of whether or not the materials of the tubular body 24 and the flaring portion 25 are the same, it is contemplated that the materials have a low metal-to-space ratio. The choice of material, however, must be such that it enables the tubular body 24 to achieve a pre-expanded 32 and a post-expanded 33 diameter (see FIGS. 2a, 3a) and to retain its pre-expanded and expanded shape. Likewise, the structural configuration must be chosen so that the ostial stent 20 possesses expansion and shape retention characteristics. It is contemplated, therefore, that the ostial stent 20 may possess a tubular structure with some geometric pattern 34 that facilitates shape retention and expansion.

Figure 4:
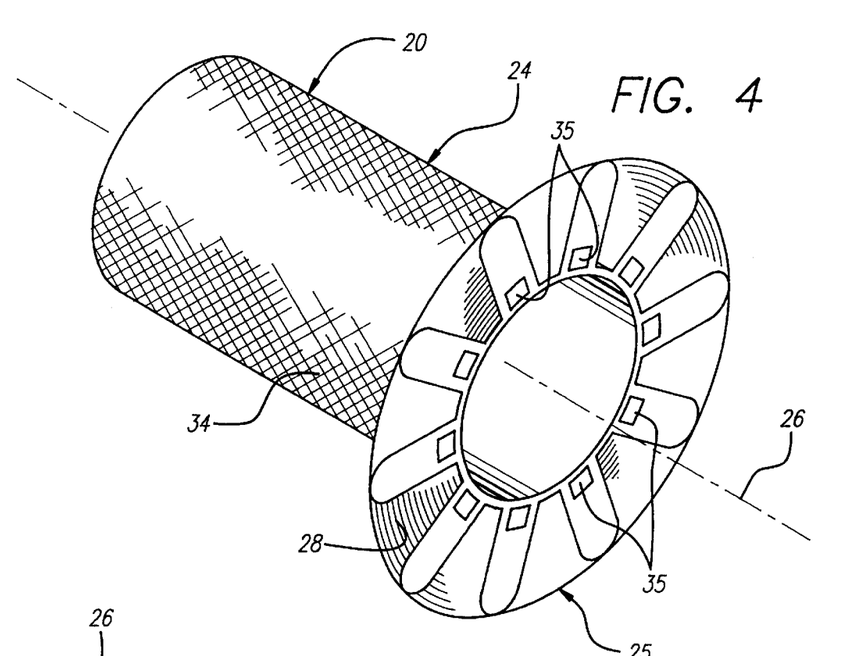
FIG. 4 depicts a perspective view of an alternate embodiment of the present invention, illustrating an ostial stent in an expanded and deformed configuration.
Figure 5:
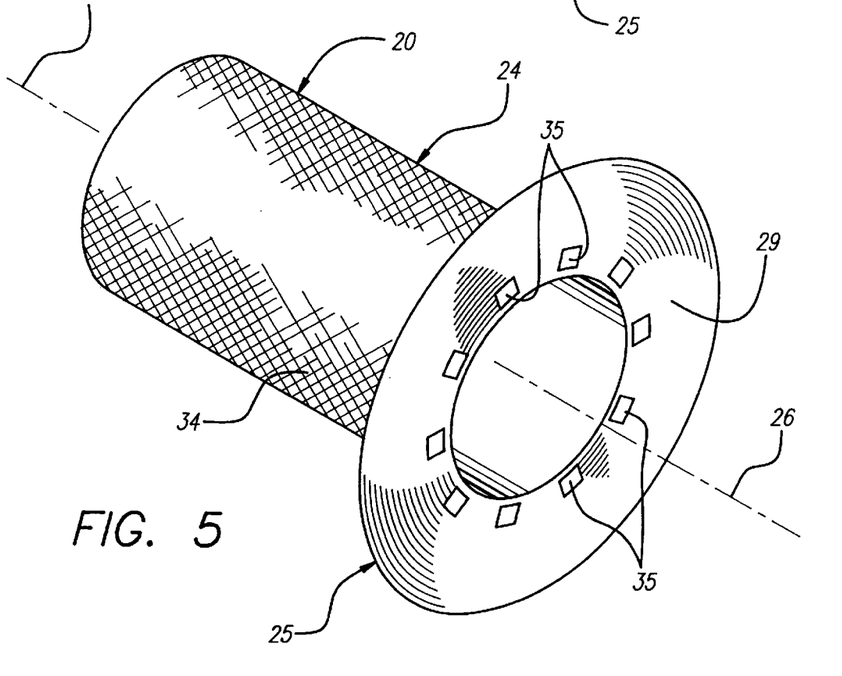
FIG. 5 depicts a perspective view of another embodiment of the present invention, illustrating an ostial stent in an expanded and deformed configuration.

The flaring portion 25 is capable of expanding and may be comprised of individual pedals 26 or in the alternative and as shown in FIGS. 4 and 5, the flaring portion 25 may comprise malleable material 28, 29 that enhances the conforming capabilities of the flaring portion. Therefore, in order to enhance conforming capabilities, the flaring portion may be comprised of pedals connected by malleable connecting material 28 or entirely of malleable material 29.

Prior to deformation, the flaring portion 25 is substantially parallel to the longitudinal axis 26 of the ostial stent 20. Upon expansion and deformation, the flaring portion is nonparallel to and at some angle slanting away from the longitudinal axis 26 of the ostial stent 20. In addition, upon deformation or flaring out, the flaring portion deforms to varying degrees along its length and substantially conforms to the ostium 30 to the diseased portion 31 of the bifurcated vessel 21 (see FIG. 6).

Radiopaque markers 35 (FIGS. 1, 2, 3, and 6) may be formed in or attached to the ostial stent 20 and their location may be selected to facilitate placement of the ostial stent 20 within a diseased bifurcated vessel 21. The radiopaque markers 35 may be located near the joining line 36 between the tubular body and flaring portion and may also be aligned with the pedals 27 comprising the flaring portion. Since the radiopaque markers 35 may be observed through the use of radiography, strategic arrangement of the radiopaque markers 35 upon or within the ostial stent 20 allows the placement of the joining line 36 between the tubular body 24 and the flaring portion 25 at or near the ostium 30 to the diseased portion 31 of a bifurcated vessel 21.

Advancement of the ostial stent 20 to the diseased portion 31 of the bifurcated vessel 21 is accomplished through the utilization of a balloon catheter 23. The balloon catheter 23 contemplated comprises the structure and features that are typical to balloon catheters found in the art. The dimensional characteristics and material of the balloon catheter 23 utilized for the advancement of the ostial stent 20 is dependent upon the application. In general, the balloon catheter 23 embodies a balloon portion 37 and a hollow, tubular member 38 extending proximally therefrom. The tubular member 38 is in fluid communication with the balloon portion 37 and thereby enables the balloon 37 with expansion and deflation capabilities. The tubular member 38 is also comprised of sufficient rigidity so that the advancement of the balloon catheter 23 and ostial stent 20 through the patient's vasculature is possible. In addition, the tubular member may embody a secondary cavity through which a guidewire (not shown) may be placed.

The balloon catheter 23 is of sufficient length to enable the delivery of the ostial stent 20 to the area of the diseased bifurcated vessel 21 and the balloon 37 of the balloon catheter 23 is capable of securely holding the ostial stent 20 during advancement and capable of expanding sufficiently to seat and cap the ostial stent 20 within the diseased vessel 21. First, the balloon catheter 22 is loaded with an unexpanded and undeformed ostial stent 20 and then entered into the patient's circulatory system through a cutdown 38. Therefore, advancement of the ostial stent 20 is achieved by applying force 40 to a portion of the tubular member 38 extending outside the patient's body.

By way of example, the ostial stent 20 is shown loaded upon the balloon catheter 23 with the flaring portion 25 at the distal end of the balloon catheter 23. It is contemplated, however, that the ostial stent 20 may be loaded with the tubular body 24 at the distal end of the balloon catheter 23 (not shown).

Figure 6:
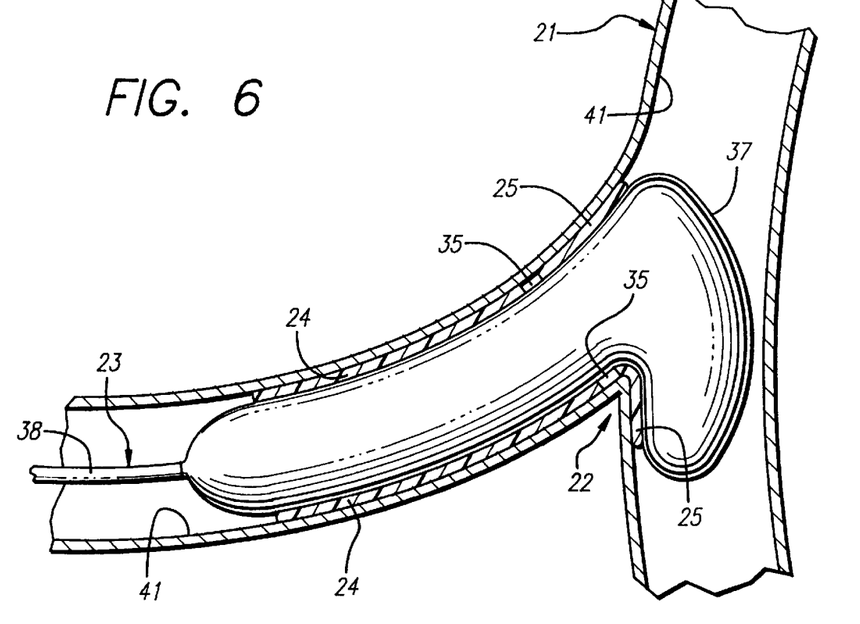
FIG. 6 depicts a partial cross-sectional view of the stent of FIGS. 2 and 3, illustrating a preferred method of expansion and deformation of an ostial stent.

Through the use of radiography, the strategically positioned radiopaque markers 35 are viewed, and the ostial stent is positioned within the diseased portion 31 of a bifurcated vessel 21 (FIG. 6). Thereafter, balloon catheter 23 is expanded, and the tubular body 24 is seated within and repairs the diseased vessel 21 and the flaring portion 25 is expanded and deformed so that the ostial stent 10 "caps" the ostium to the diseased portion 31 of the vessel 21. Where the ostial stent 20 properly "caps" the ostium 30 to the diseased portion of the bifurcated vessel 21, the flaring portion 25 substantially conforms to the vessel walls 41 comprising the bifurcation 22, thereby allowing for unobstructed flow of blood through the bifurcated vessel. Although the seating of the tubular body 24 and "capping" of the flaring portion 25 may be accomplished contemporaneously, it may be preferred that one follow the other. Additionally, in order to properly repair the diseased vessel, the length of the tubular body 24 is selected so that the entire diseased portion 31 extending away from the ostium 30 is repaired and the length of the flaring portion 25 is selected so that it repairs, upon deformation, the entire diseased area 31 at the ostium 30 to the bifurcation 22.

Figure 7:
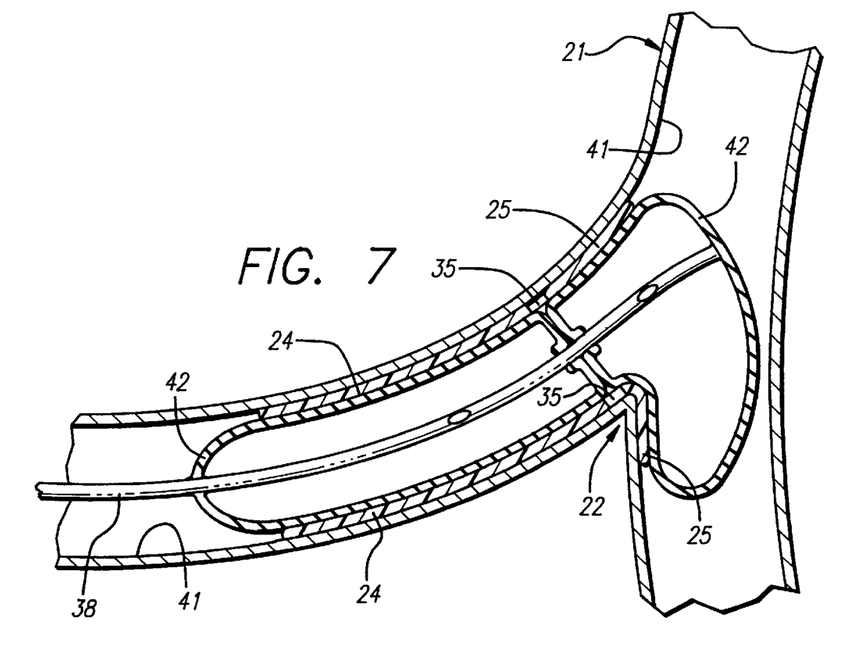
FIG. 7 depicts a partial cross-sectional view of the stent of FIGS. 2 and 3, illustrating an alternate method of expansion and deformation of an ostial stent.
Figure 8:
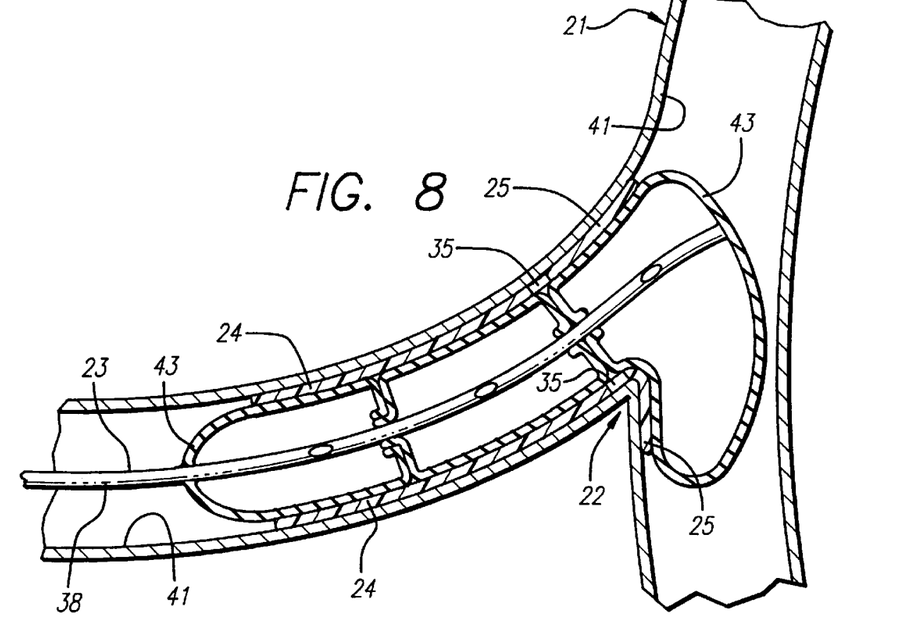
FIG. 8 depicts a partial cross-sectional view of the stent of FIGS. 2 and 3, illustrating another method of expansion and deformation of an ostial stent.

It is also contemplated that expansion and deformation of the ostial stent 20 can be accomplished through the use of a series of various sized and shaped balloons or by means of bi-balloon 42 or tri-balloon 43 catheter structures where the various sections of the balloon catheter act to carry the ostial stent 20, seat the tubular body 24 and deform the flaring portion (FIGS. 7 and 8). Irrespective of the mechanism employed, it is the seating within and "capping" of the ostium 30 to the diseased portion 31 of the bifurcated vessel 21 that must be achieved.

Once the ostial stent 20 is properly seated and "capped" within the bifurcated vessel 21, the diseased vessel 21 is completely repaired and blood is not obstructed in any portion of the bifurcation 22. The balloon catheter 23 can then be removed through the cutdown 39, and the cutdown 39 can be closed. Thereafter, the repair site is available for further interventional treatment should it be necessary.

In another embodiment, an ostial stent 44 (not shown) can be comprised of a memory-retaining material such as NiTi. At a cold temperature, the ostial stent 44 would be unexpanded and undeformed. At an increased temperature, the ostial stent 44 would have an expanded and deformed configuration. During transport, the cold temperature of the ostial stent 44 could be maintained. Upon arrival at the diseased area, the stent 44 could be subjected to an increased temperature and allow the ostial stent 44 to deform and expand, thereby capping and seating the ostial stent 44 within a bifurcation. The deformed and expanded configuration would be retained at normal body temperature.

Advancement of the memory-retaining ostial stent 44 is also contemplated to be accomplished by means of a balloon catheter. In order to maintain the unexpanded and undeformed shape configuration of the memory-retaining ostial stent 44, the balloon catheter could provide means to maintain the cold temperature of the ostial stent 44. One means contemplated is loading the balloon catheter carrying the memory-retaining ostial stent 44 with a compound having a cold temperature. The cold compound could then be removed and replaced with a high-temperature compound. The high-temperature compound would cause the memory-retaining ostial stent 44 to deform and expand, thereby seating within and capping a diseased vessel.

It is also contemplated that only a portion of the ostial stent 44 be comprised of a memory-retaining material. For this stent, balloon expansion can be utilized to expand or deform a portion of the stent that was not comprised of a memory-retaining material.

Figure 9:
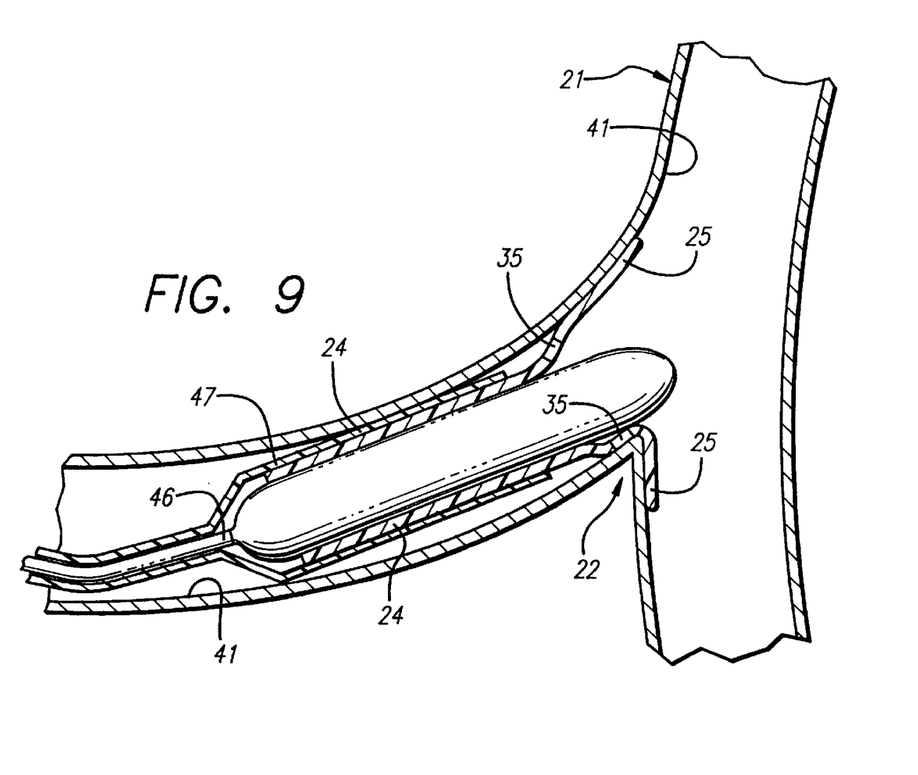
FIG. 9 depicts a partial cross-sectional view of a stent comprising spring-like material, illustrating a method of expansion and deformation of an ostial stent comprising spring-like material.

In another embodiment, an ostial stent 45 is comprised of spring-like material (FIG. 9). Advancement of the spring-like ostial stent 45 is accomplished by a balloon catheter 46. In this embodiment, a retaining sleeve 47 is employed to maintain the spring-like ostial stent 45 in its unexpanded and undeformed configuration. Upon arrival of the spring ostial stent 45 at the repair site, removal of the retaining sleeve 47 allows the spring-like ostial stent 45 to spring to its expanded and deformed configuration, thereby seating and "capping" a diseased vessel 21 at a bifurcation 27.

It is also contemplated that only a portion of the spring ostial stent 45 be comprised of spring-like material. Thus, deformation or expansion of the portion that is not comprised of spring-like material can be accomplished by a balloon catheter.

From the foregoing, it will be appreciated that the ostial stent of the invention allows complete repair of a diseased vessel of a bifurcation and provides a method and apparatus for accomplishing the same. It will also be appreciated that proper seating and "capping" of the ostial stent 20 within a diseased, bifurcated vessel 21 achieves reparation without obstructing the flow of blood at the site of the bifurcation.

While several particular forms of the invention have been illustrated and described, it will also be apparent that various modifications can be made without departing from the spirit and scope of the invention. Thus, it should be understood that various changes in form, detail, and application of the present invention may be made without departing from the spirit and scope of this invention.

I claim:

1. A method for repairing a bifurcated vessel, wherein a first portion of the vessel opens into a second portion of said vessel, and wherein said first portion has a diseased area adjacent an ostium defining the intersection between said first and second portions, a stent having a tubular body and a flaring portion, means for expanding said tubular body and expanding and deforming said flaring portion, said expansion means operating to expand said tubular body and said flaring portion from an unexpanded and undeformed to an expanded and deformed configuration, the method comprising:

loading said tubular body and said flaring portion in said unexpanded and undeformed configuration upon a balloon portion of a catheter;

advancing said balloon catheter and said tubular body through a patient's vasculature to said diseased area of said bifurcated vessel such that said tubular body is positioned within said first portion, while said flaring portion extends from said ostium to partially protrude into said second portion;

expanding said balloon portion of said catheter to expand said tubular body from said unexpanded to said expanded configuration, and capping the ostium by expanding and deforming said flaring portion from said unexpanded and undeformed to said expanded and deformed configuration; and removing said balloon catheter from the patient's vasculature.

2. A method for repairing a bifurcated vessel, wherein a first portion of the vessel opens into a second portion of said vessel, and wherein said first portion has a diseased area adjacent an ostium defining the intersection between said first and second portions, a stent having a tubular body and a flaring portion, means for expanding said tubular body and expanding and deforming said flaring portion, said expansion means operating to expand said tubular body from an unexpanded to an expanded configuration, and means for expanding said flaring portion from an unexpanded and undeformed to an expanded and deformed configuration, the method comprising:

loading said tubular body comprising a memory-retaining material at a temperature below normal body temperature upon a balloon portion of a catheter, said tubular body having said unexpanded configuration and said flaring portion having said unexpanded and undeformed configuration at said temperature below normal body temperature;

advancing said balloon through a patient's vasculature to said diseased area of said bifurcated vessel and positioning said tubular body within said first portion, said flaring portion extending from said ostium to partially protrude into said second portion;

increasing the temperature of said memory-retaining material to a temperature at or above body temperature thereby expanding said tubular body from said unexpanded to said expanded configuration and capping the ostium by expanding and deforming said flaring portion; and     removing said balloon portion and catheter from the patient's vasculature.

\* \* \* \* \*

UNITED STATES PATENT AND TRADEMARK OFFICE
CERTIFICATE OF CORRECTION

PATENT NO. : 5,868,777
DATED : Feb. 9, 1999
INVENTOR(S) : Sharon Lam

It is certified that error appears in the above-identified patent and that said Letters Patent is hereby corrected as shown below:

Title page under References Cited, item [56] add the following:

```
--5,156,619   10/1992   Ehrenfeld
  5,507,769    4/1996   Martin et al.
  5,562,726   10/1996   Chuter
  5,571,167   11/1996   Masginot
  5,571,170   11/1996   Palmaz, et al.
  5,571,171   11/1996   Barone
  5,571,173   11/1996   Parodi
  5,575,817   11/1996   Martin
  5,578,071   11/1996   Parodi
  5,578,072   11/1996   Barone et al.
  5,591,228    1/1997   Edoga
  5,591,229    1/1997   Parodi
  5,613,980    3/1997   Chauhan
  5,617,878    4/1997   Taheri--.
```

Signed and Sealed this

Eighth Day of June, 1999

Attest:

Q. TODD DICKINSON

*Attesting Officer*      *Acting Commissioner of Patents and Trademarks*

UNITED STATES PATENT AND TRADEMARK OFFICE
CERTIFICATE OF CORRECTION

PATENT NO. : 5,868,777
DATED : Feb. 9, 1999
INVENTOR(S) : Sharon Lam

It is certified that error appears in the above-identified patent and that said Letters Patent is hereby corrected as shown below:

Column 6, line 53, change "22",
to read --23--.

Signed and Sealed this

Twenty-first Day of September, 1999

Attest:

Q. TODD DICKINSON

*Attesting Officer*          *Acting Commissioner of Patents and Trademarks*